US00PP08815P

United States Patent [19]

Moore

[11] Patent Number: Plant 8,815

[45] Date of Patent: Jul. 5, 1994

[54] MINIATURE ROSE PLANT NAMED 'MORDASHIN'

[76] Inventor: Ralph S. Moore, 2519 E Noble Ave., Visalia, Calif. 93277

[21] Appl. No.: 992,819

[22] Filed: Dec. 14, 1992

[51] Int. Cl.[5] ..... A01H 5/00

[52] U.S. Cl. ..... Plt./7.1

[58] Field of Search ..... Plt. 7.1

[56] References Cited

U.S. PATENT DOCUMENTS 5487 6/1985 Saville ..... Plt. 7

7058 11/1989 Saville ..... Plt. 7

*Primary Examiner*—Howard J. Locker

*Assistant Examiner*—Elizabeth C. Kemmerer

[57] ABSTRACT

This invention relates to a new and distinct cultivar of miniature rose plant primarily identified by its very double flowers with the petals being yellow blended with red with a yellow reverse.

1 Drawing Sheet

1

The present invention relates to a new and distinct cultivar of hardy, dwarf, bush type rose plant of the miniature class; the cultivar being primarily characterized—as to novelty—by the very double flowers, the petals being generally deep yellow tipped with red.

The cultivar is further characterized by:

An abundance of bloom, with flowers usually borne singly.

Little or no fragrance.

A plant which is vigorous, of rounded to upright shape with small semi-glossy to matte foliage with pointed leaflets; the buds and flowers being similar in form to Rise'N Shine (miniature—U.S. Plant Pat. No. 4,231) but differing in color, being yellow edged and/or blended with red.

The plant, which has a normal height of 14–16 inches, can easily be maintained at lesser height by occasional trimming.

A plant which grows and blooms satisfactorily both in greenhouse and outdoors; is good for growing in pots; and provides excellent garden decoration as well as cut flowers.

The present cultivar of miniature rose was originated by me at my nursery, located at Visalia, Calif., under conditions of careful control and observation, as a cross between Little Darling (Floribunda—U.S. Plant Pat. No. 1,581) as the seed parent and Rise'N Shine (miniature—Plant Pat. No. 4,231) as the pollen parent.

Subsequent to origination of the cultivar I successfully asexually reproduced it at the same nursery, located as aforesaid, by budding as well as by cuttings; the reproductions having run true in all respects.

The color photograph illustrates the cultivar including the foliage, buds and flowers.

Referring now specifically to the new and distinct cultivar of miniature rose plant, the following is a detailed description thereof in outline; all major color plate identifications being by reference to The Royal Horticultural Society Colour Chart, except where common terms of color definition are employed.

Type: Hardy; dwarf; bushy; upright; seedling; greenhouse; outdoors; cut flowers; garden decoration; potted plant.

Class: Miniature. Cultivar identification: MORdashin (Commercial synonym: Southern Delight).

Flowers borne: Usually singly or occasionally in loose clusters on sturdy, wirey stems.

2

Quantity of bloom: Abundant both outside and in greenhouse.

Bud:

*Peduncle.*—Medium length; slender but sturdy; erect; medium green, sometimes tinted bronze (outdoors); nearly smooth.

*Before calyx breaks.*—Size — small. Form — pointed, with several small foliaceous appendages on surface of bud; with foliaceous parts extending beyond the tip of the bud equal to more than one-half of its length. Color — medium green, occasionally tinted with bronze (outdoors).

*As calyx breaks.*—Color — yellow with red on petal tip and petal edge.

*Opening.*—Opens well in all weather.

Bloom:

*Size when fully open.*—Small, averaging about 40 mm (1¾").

*Petalage.*—Double — averaging about 40 (or more) petals, arranged regularly plus several small petaolids.

*Form.*—Full, high centered — first becoming rounded with petals rolled loosly outward and downward. Open flowers usually show stamens.

*Sepals.*—Permanent; spear shaped; recurved.

Petals: Fairly thick; satiny on inside and on outside surface.

*Shape.*—Outside petals, broad lanceolate (wedge shaped) with small acute tip; Intermediate — broad lanceolate with nearly round or short acute tip; Inside — lanceolate with acute tip.

Color: Newly opened flower from a plant grown in plastic greenhouse (October 1992), Visalia, Calif. (Photo: flowers from similar plants, Aug., 1993):

*Outside petal.*—Outside surface — yellow (near Yellow Group 9B). Inside surface — near Yellow Group 9A at base blending into yellow tinted with red on upper ⅓ of petal. Red color similar to Red Group 43B with the red sometimes blending or bleeding into the yellow color.

*Intermediate petal.*—Outside surface similar to outside petal. Inside surface similar to outside petal.

*Inner petal.*—Outside surface similar to intermediate petal; inside surface — similar to intermediate petal. General color effect; newly opened flowers — yellow brushed with red (a red on yellow effect). Three days open — color — similar to fresh open flower, but less bright. Behavior — opens well in all weather. Spent petals or flowers drop off. Flower longevity (July–August 1992) — plant in pot 4–6 days or longer. Cut flowers at living room temperature 4–5 days or longer.

Reproductive organs:

*Stamens.*—Abundant, arranged regularly about pistil.

*Filaments.*—Fairly short, yellow.

*Anthers.*—Well formed, yellow.

*Pollen.*—Moderate.

*Pistils.*—Average number.

*Styles.*—Long; reddish; bunched.

*Ovaries.*—All enclosed in calyx.

*Hips.*—Usually none.

*Seed.*—None.

Foliage:

*Leaves.*—Compound of five (sometimes three or seven) leaflets; medium small; leathery; semi-glossy.

*Leaflets.*—Shape: broad lanceolate; apex acute; base — rounded. Color: medium green (can be as dark as Green 147-A but usually lighter green); new growth — normal (medium) green (sometimes tinted reddish). Rachis: medium strength; upper side smooth; grooved; underside may have several small thorns (or claws). Stipules: medium to short length; medium width; medium to short length narrow points which turn out usually at about 45 degrees or more. Color similar to leaflets.

Growth:

*Habit.*—Dwarf; bushy; upright; much branched.

*Growth.*—Vigorous; internodes short.

*Canes.*—Medium slender; sturdy.

*Main stems.*—Color: medium green.

*Thorns.*—Average, of varying size and length — slightly inclined downward. Hairs — few or none.

The miniature rose plant and its flowers as herein described may vary in slight detail due to climatic, soil and cultural conditions under which the cultivar may be grown; the present description being of the cultivar as grown at Visalia, Calif.

The following is claimed:

1. A new and distinct cultivar of miniature rose plant of hardy, dwarf, bushy, upright, much branched habit, substantially as illustrated and described, characterized by buds and flowers, basically yellow and edged with red, with the reverse being yellow, the bud being pointed in the early opening stage, resembling in form Rise'N Shine (miniature — U.S. Plant Pat. No. 4,231) with the open flower being very double and rounded with 40 or more petals; and further characterized by a plant of compact, vigorous, upright shape with main stems and shoots with less than average thorniness, the said plant being easy to propagate from soft wood cuttings with an abundance of small semi-glossy foliage, the flowers being usually borne singly on medium length stems.

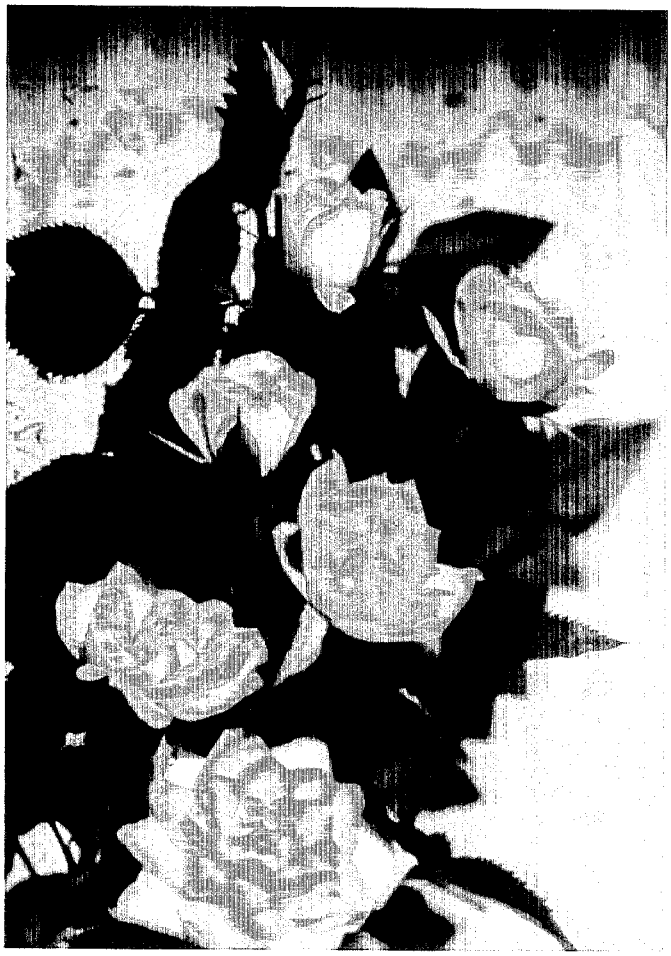

* * * * *